(12) United States Patent
Lin et al.

(10) Patent No.: US 11,866,393 B2
(45) Date of Patent: Jan. 9, 2024

(54) 7,7'-DIHALO-3,3,3',3'-TETRAMETHYL-1,1'-SPIROBIINDANE AND PREPARATION METHOD THEREOF

(71) Applicant: ZHEJIANG UNIVERSITY, Hangzhou (CN)

(72) Inventors: Xufeng Lin, Hangzhou (CN); Linxi Yao, Hangzhou (CN); Shirui Chang, Hangzhou (CN); Lei Wang, Hangzhou (CN)

(73) Assignee: Zhejiang University, Zhejiang (CN)

( * ) Notice: Subject to any disclaimer, the term of this patent is extended or adjusted under 35 U.S.C. 154(b) by 18 days.

(21) Appl. No.: 17/700,500

(22) Filed: Mar. 22, 2022

(65) Prior Publication Data

US 2022/0213011 A1 Jul. 7, 2022

Related U.S. Application Data

(63) Continuation-in-part of application No. 16/770,956, filed as application No. PCT/CN2017/116105 on Dec. 14, 2017, now Pat. No. 11,530,230.

(51) Int. Cl.
C07C 25/22 (2006.01)
C07C 17/013 (2006.01)

(52) U.S. Cl.
CPC ............ *C07C 25/22* (2013.01); *C07C 17/013* (2013.01); *C07C 2602/08* (2017.05)

(58) Field of Classification Search
None
See application file for complete search history.

(56) References Cited

FOREIGN PATENT DOCUMENTS

JP 2006080272 A * 3/2006 ............. Y02B 20/00

* cited by examiner

*Primary Examiner* — Joseph R Kosack
(74) *Attorney, Agent, or Firm* — SWOPE & YUYANG IP LAW GROUP

(57) ABSTRACT

Disclosed are 7,7'-dihalo-3,3,3',3'-tetramethyl-1,1'-spirobiindane and a preparation method thereof. The 7,7'-dihalo-3,3,3',3'-tetramethyl-1,1'-spirobiindane is a compound represented by formula I, or an enantiomer, a raceme or a diastereomer thereof. The compound of formula I could be prepared by using a racemic or optically active 3,3,3',3'-tetramethyl-1,1'-spirobiindane-6,6'-diol as a raw material through a series of reactions. The 7,7'-dihalo-3,3,3',3'-tetramethyl-1,1'-spirobiindane is a key intermediate for preparing 3,3,3',3'-tetramethyl-1,1'-spirobiindane-based phosphine ligand compounds represented by formula II or III.

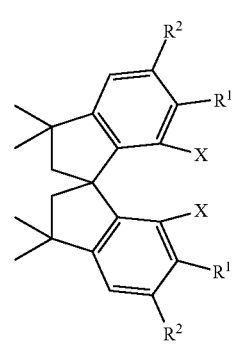

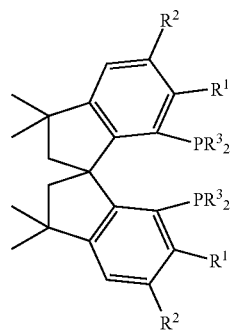

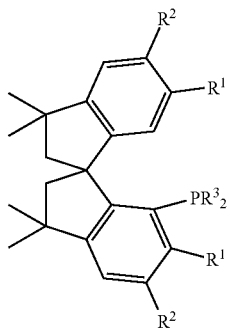

3 Claims, No Drawings

7,7'-DIHALO-3,3,3',3'-TETRAMETHYL-1,1'-SPIROBIINDANE AND PREPARATION METHOD THEREOF

TECHNICAL FIELD

The present application relates to the technical field of organic chemistry, and specifically relates to a novel 7,7'-dihalo-3,3,3',3'-tetramethyl-1,1'-spirobiindane and a preparation method thereof. The compound could be used for preparing 3,3,3',3'-tetramethyl-1,1'-spirobiindane-based phosphine ligand compounds.

BACKGROUND

It was reported in 1962 that 3,3,3',3'-tetramethyl-1,1'-spirobiindane-6,6'-diol (MSPINOL) could be obtained with high yields through acid catalysis directly from bisphenol products. Later, modified large-scale preparation methods and chiral resolution methods were reported (see the following reaction equation, *J. Chem. Soc.*, 1962, 415-418; *Org. Lett.*, 2004, 6, 2341-2343; US2006/0020150; U.S. Pat. No. 4,879,421; and *Bull. Chem. Soc. Japan*, 1977, 44, 496-505).

3,3,3',3'-tetramethyl-1,1'-spirobiindane-6,6'-diol and derivatives thereof are reported mainly for preparing polymers, but they have not been used for the preparation or application of any ligand. The corresponding raw material, bisphenol, is very cheap and can be prepared by a condensation reaction of acetone and phenol or derivatives thereof. In addition, many industrial bisphenol products (bisphenol A, bisphenol C, etc.) are available and on large-scale sales. For example, the annually produced and sold bisphenol A all over the world is up to more than 3 million tons, with a price less than 10,000 RMB per ton. The present application is intended to utilize the cheap and easily available 3,3,3',3'-tetramethyl-1,1'-spirobiindane-6,6'-diol to design and prepare a key intermediate of corresponding 3,3,3',3'-tetramethyl-1,1'-spirobiindane-based phosphine ligands. Typically, based on the method disclosed in the present application, the key intermediate of the 3,3,3',3'-tetramethyl-1,1'-spirobiindane-based phosphine ligands is prepared with the industrial large-tonnage raw material bisphenol via a four-step synthesis reaction scheme:

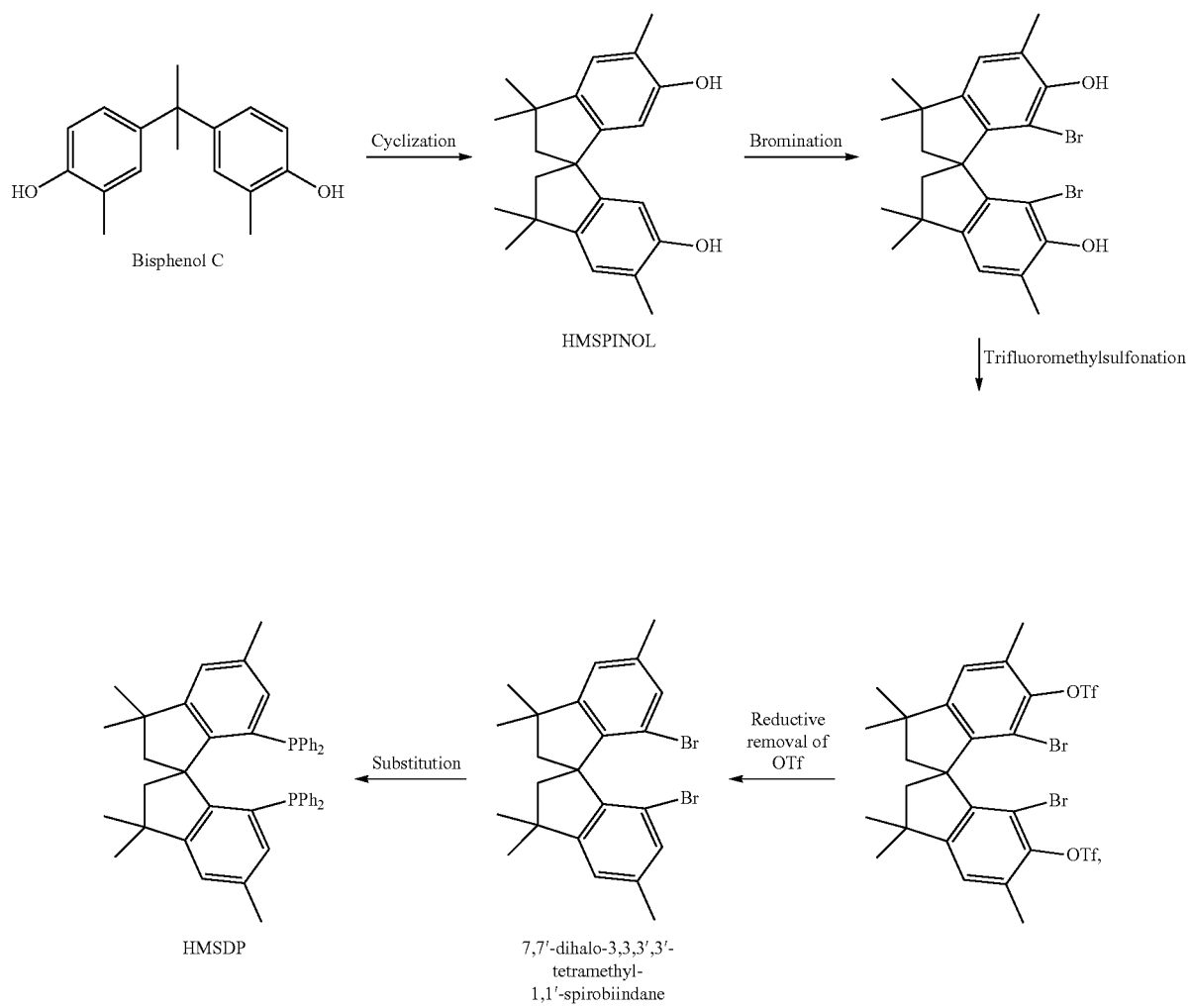

or via a six-step synthesis reaction scheme:

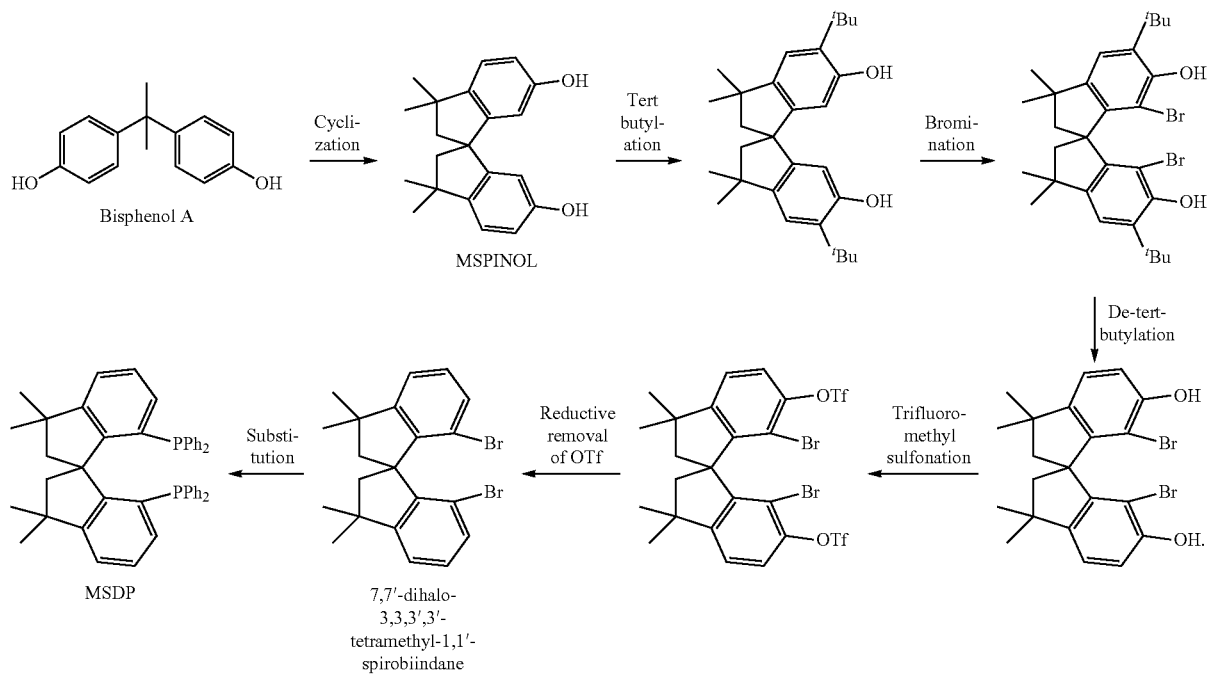

SUMMARY

An object of the present application is to provide a 7,7'-dihalo-3,3,3',3'-tetramethyl-1,1'-spirobiindane, which is a key intermediate of 3,3,3',3'-tetramethyl-1,1'-spirobiindane-based phosphine ligand compounds, and a preparation method thereof.

Provided herein is 7,7'-dihalo-3,3,3',3'-tetramethyl-1,1'-spirobiindane, which is a compound represented by formula I, or an enantiomer, a raceme or a diastereomer thereof:

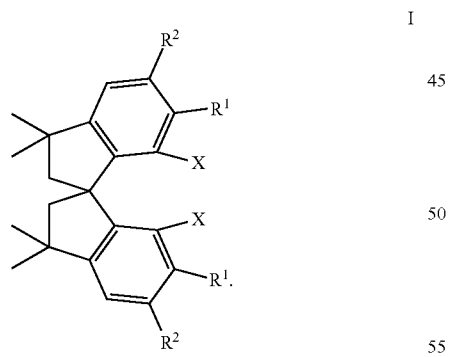

I wherein, $R^1$ is selected from the group consisting of hydrogen, $C_1$-$C_{10}$ alkyl or perfluoroalkyl, $C_3$-$C_6$ cycloalkyl, aryl or substituted aryl, and heteroaryl or substituted heteroaryl; $R^2$ is selected from the group consisting of hydrogen, $C_1$-$C_{10}$ alkyl or perfluoroalkyl, and $C_3$-$C_6$ cycloalkyl; wherein the substituted aryl or the substituted heteroaryl has one or more substituents independently selected from the group consisting of halogen, $C_1$-$C_4$ alkyl or perfluoroalkyl, $C_3$-$C_6$ cycloalkyl, $C_1$-$C_4$ alkoxy or perfluoroalkoxy, methylenedioxy, aryl, aryloxy, and heteroaryl; the heteroaryl is $C_5$-$C_{14}$ heteroaryl; and X is halogen.

Further, the compound represented by formula I may be any one of the following compounds:

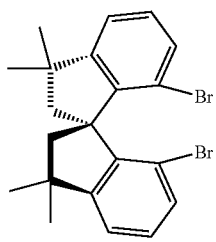

III-a

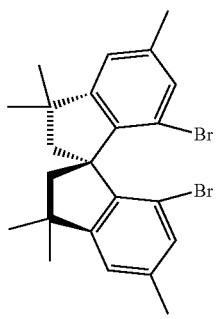

III-b

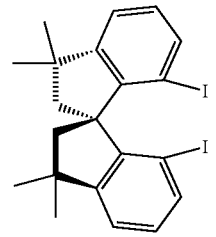

III-c

III-d

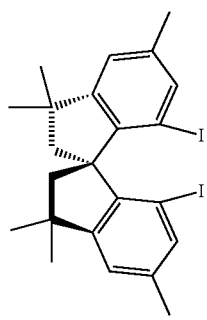

III-ee

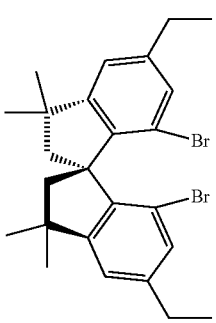

III-ff

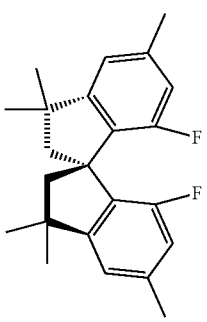

III-gg

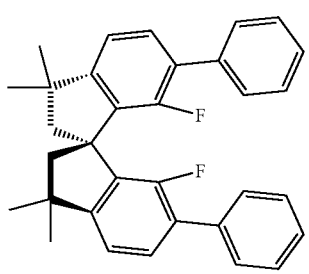

III-hh

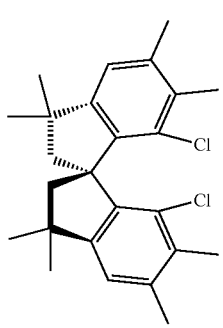

III-i

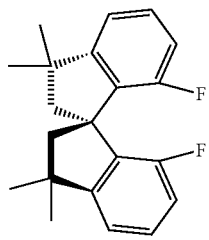

III-j

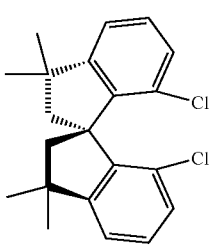

III-kk

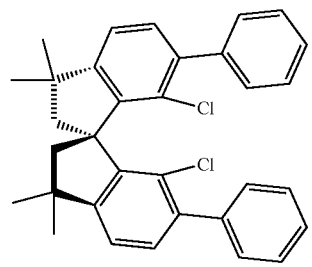

III-l

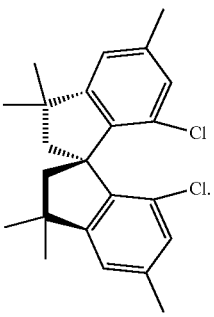

The compound represented by formula I could be prepared by using a racemic or optically active 3,3,3',3'-tetramethyl-1,1'-spirobiindane-6,6'-diol (formula 1) as a raw material, through the following processes:

Under the condition that $R^2$ is selected from $C_1$-$C_{10}$ alkyl or perfluoroalkyl and $C_3$-$C_6$ cycloalkyl, the compound represented by formula I is prepared as follows: the compound represented by formula 1 is first subjected to a halogenation reaction to obtain a compound 2, the compound 2 is subjected to esterification with trifluoromethanesulfonic anhydride to obtain a compound 3, and then the compound 3 is subjected to a palladium-catalyzed coupling reaction or a reduction reaction to obtain the compound represented by formula I;

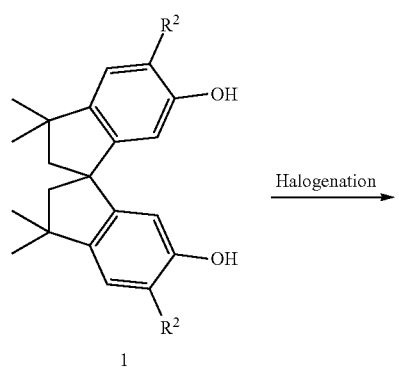

1

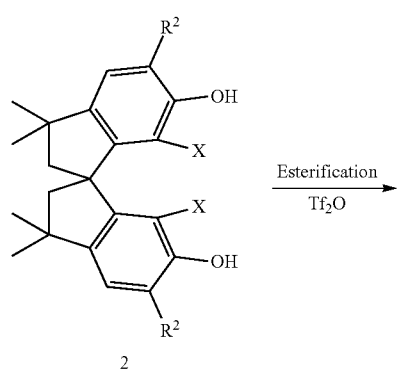

2

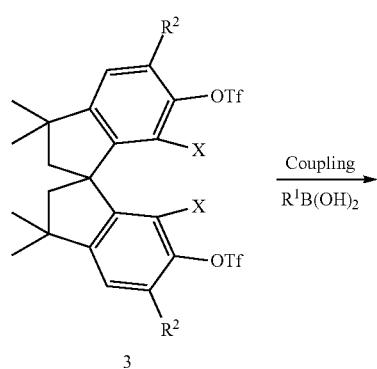

3

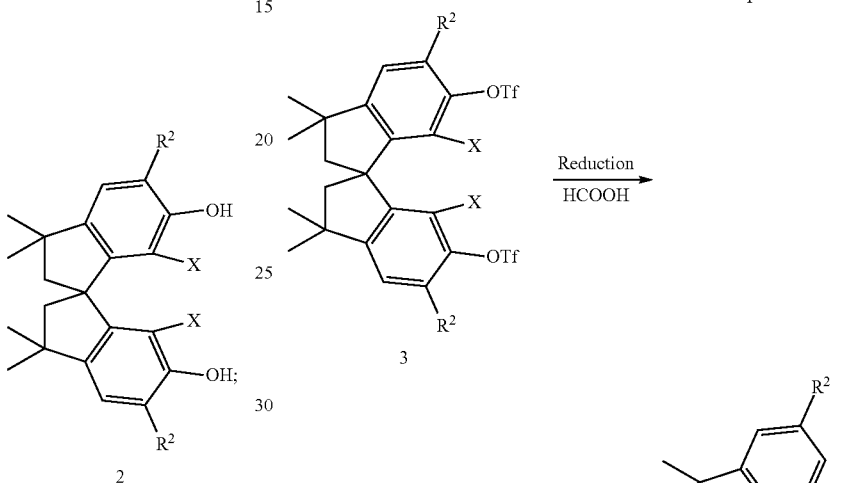

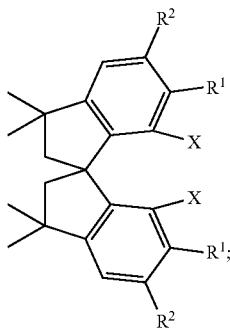

I

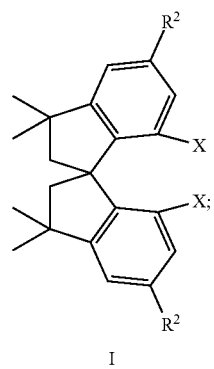

I wherein the process of the halogenation reaction for preparing the compound 2 from the compound 1 is that in dichloromethane or ethyl acetate, the compound 1 reacts with a halogenation reagent for 12-24 hours under catalysis of p-toluenesulfonic acid and at a temperature of 0° C. to 40° C., to obtain the intermediate 2, in which the molar ratio of the compound 1, the halogenation reagent and the p-toluenesulfonic acid is typically 1:2-4:0-1; the halogenation reagent may be N-halosuccinimide, dibromohydantoin, iodine chloride, bromine, chlorine gas, or N-fluorodiphenyl sulfonamide;

the process of the esterification for preparing the compound 3 from the compound 2 is that in dichloromethane or dichloroethane, the compound 2 reacts with trifluoromethanesulfonic anhydride for 0.2-6 hours in the presence of an alkali at a temperature of 0° C. to 40° C., to obtain the compound 3, in which the alkali is one selected from the group consisting of pyridine, triethylamine, potassium hydroxide, and sodium hydroxide, or a combination thereof in any ratio, and the molar ratio of the compound 2, the alkali and the trifluoromethanesulfonic anhydride is 1:2-8:2-6;

the process of the selective reduction reaction for preparing the compound I from the compound 3 is that in N,N- dimethylformamide, dioxane or dimethyl sulfoxide, in the presence of an organic alkali, using bis(triphenylphosphine) palladium dichloride and 1,3-bis(diphenylphosphino)propane as a catalyst system, the compound 3 reacts with formic acid for 1-6 hours at a temperature of 25° C. to 100° C., to obtain the compound I, in which the molar ratio of the compound 3, the formic acid, the organic alkali, the bis(triphenylphosphine) palladium dichloride and the 1,3-bis(diphenylphosphino)propane is 1:2-6:8-15:0.05-0.2:0.05-0.2; and the organic alkali is triethylamine, tripropylamine or tributylamine; and the process of the coupling reaction for preparing the compound I from the compound 3 is that in N,N-dimethylformamide, dioxane, water, acetone, dimethyl sulfoxide or a mixed solvent thereof in any ratio, in the presence of an alkali and a metal catalyst, the compound 3 reacts with a coupling reagent $R^1B(OH)_2$ for 6-36 hours at a temperature of 25° C. to 100° C., to obtain the compound represented by formula I, in which the alkali is one selected from the group consisting of potassium hydroxide, sodium hydroxide, potassium carbonate, cesium carbonate, and sodium carbonate, or a combination thereof in any ratio; the molar ratio of the compound 3, the alkali and the metal catalyst is 1:0.1-5:0.05-0.2; the molar ratio of the compound 3 to the coupling reagent $R^1B(OH)_2$ is 1:2-4; and the metal catalyst is at least one of selected from the group consisting of $Pd(OAc)_2$, $Pd(PPh_3)_4$, $PdCl_2$, $Pd(PPh_3)_2Cl_2$, $Pd_2(dba)_3$, CuI, and dpppNiCl$_2$, or a combination thereof in any ratio.

Under the condition that $R^2$ is hydrogen, the compound represented by formula I is prepared as follows: the compound represented by formula 1 is first subjected to a tert-butylation reaction to obtain a compound A1, the compound A1 is subjected to a halogenation reaction to obtain a compound 4, the compound 4 is subjected to a tert-butyl elimination reaction to obtain a compound 5, the compound 5 is subjected to esterification with trifluoromethanesulfonic anhydride to obtain a compound 6, and then the compound 6 is subjected to a palladium-catalyzed coupling reaction or a reduction reaction to obtain the compound represented by formula I;

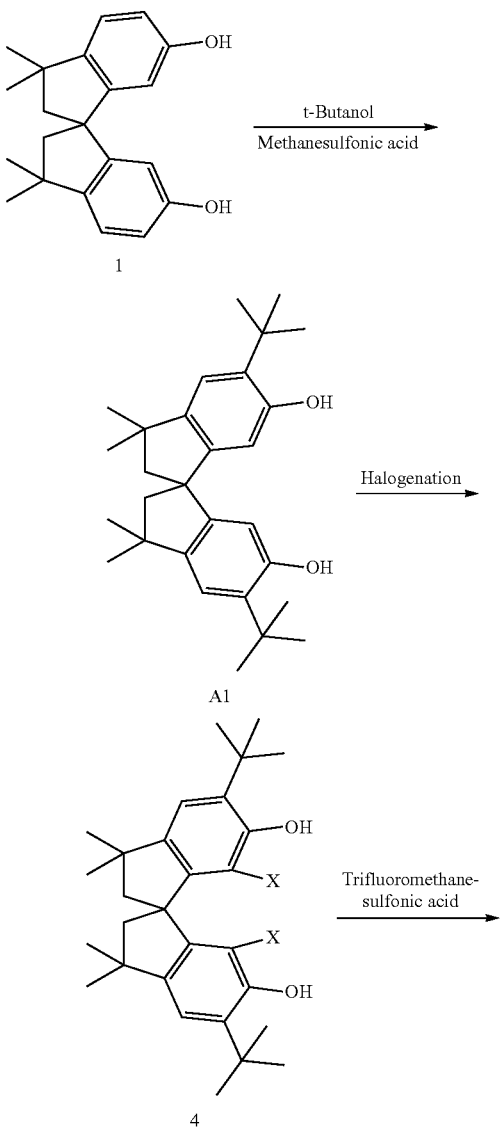

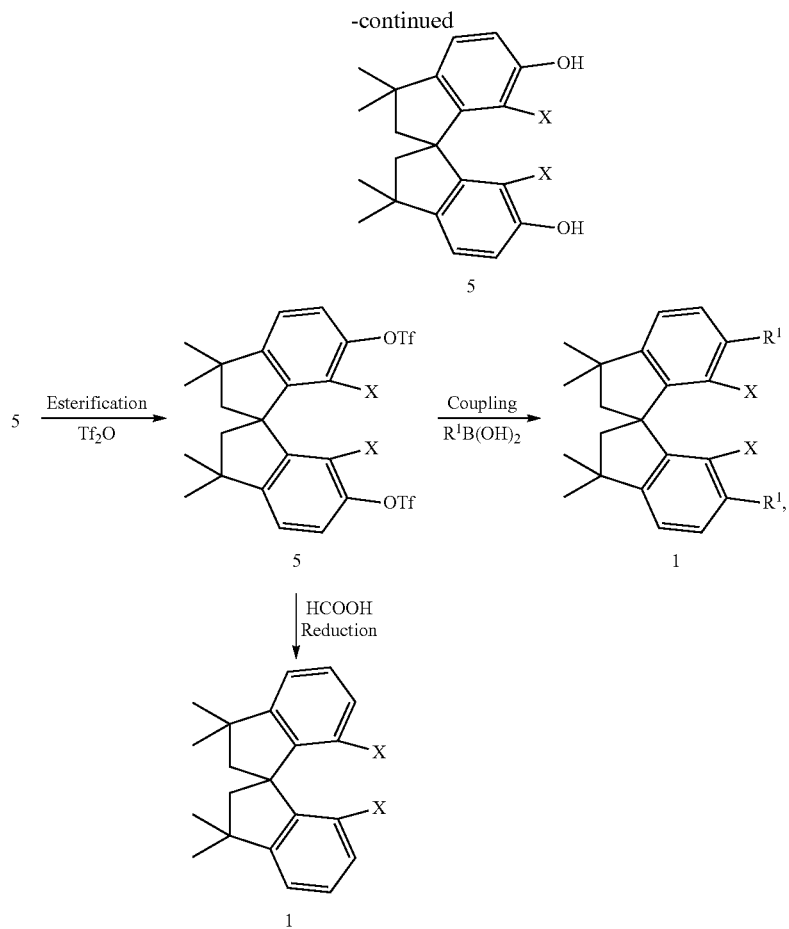

wherein X is halogen.

Detailed synthesis method is as follows: under the condition that $R^2$ is hydrogen, the process of preparing the compound 5 from the compound 1 is that in dichloromethane or chloroform, in the presence of methanesulfonic acid, the compound 1 reacts with tert-butanol for 2-6 hours at temperature of 0° C. to 40° C., to obtain the intermediate A1; in dichloromethane or ethyl acetate, the intermediate A1 reacts with a halogenation reagent under the catalysis of p-toluenesulfonic acid for 12-24 hours at a temperature of 0° C. to 40° C., to obtain the intermediate 4; and in toluene or dichloromethane, the intermediate 4 is treated with trifluoromethanesulfonic acid for 1-48 hours to obtain the intermediate 5; in which the molar ratio of the compound 1, the tert-butanol and the methanesulfonic acid is 1:2-4:5-12, the molar ratio of the intermediate A1, the halogenation reagent and the p-toluenesulfonic acid is 1:2-4:0-1, and the molar ratio of the intermediate 4 to the trifluoromethanesulfonic acid is 1:0.8-3; the halogenation reagent may be N-halosuccinimide, dibromohydantoin, iodine chloride, bromine, chlorine gas, or N-fluorodiphenylsulfonamide; and the subsequent esterification, coupling and reduction reaction processes are similar to the above.

The use of the compound I of the present application is to prepare a compound of formula II by using the racemic or optically active compound of formula I as a raw material through a double substitution reaction with a disubstituted phosphine halide under the action of alkali, the compound of formula II being useful as a phosphine ligand; or to prepare a compound of formula III by using the racemic or optically active compound of formula I as a raw material through a monosubstitution reaction with a disubstituted phosphine halide under the action of alkali, the compound of formula III being useful as a phosphine ligand or an organic catalyst.

II

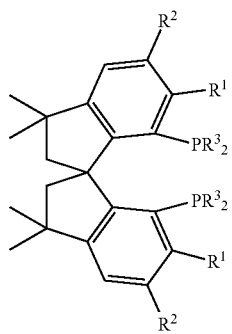

-continued

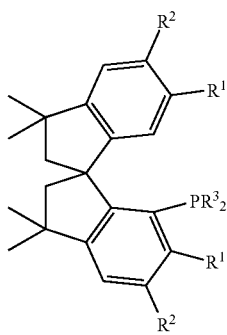

III

DETAILED DESCRIPTION OF THE EMBODIMENTS

The following examples are provided to facilitate the understanding of the present application, but are not intended to limit to the scope of the present application.

Example 1

Synthesis of (R)-3,3,3',3'-tetramethyl-7,7'-dibromo-1,1'-spirobiindane ((R)-III-a)

15.4 g of the compound (R)-MSPINOL (with a molecular weight of 308, 0.05 mol), 15 mL of tert-butanol (0.156 mol), and 180 mL of dichloromethane were added to a reaction flask. After stirring evenly (to be a suspension), 27 mL of methanesulfonic acid (0.41 mol) was added dropwise under an ice-water bath, and the turbidity gradually disappeared. The reaction solution became turbid again when the ice-water bath was removed after the addition. After stirring for another 2 hours, the reaction was quenched by adding 100 mL of ice water. The reaction solution was evaporated under reduced pressure to remove dichloromethane, and then at least 200 mL of ethyl acetate was added under stirring to dissolve all precipitates. The liquid was separated, in which the aqueous phase was extracted with ethyl acetate, and the organic phases were combined. The organic phase was washed with saturated sodium chloride solution, dried over anhydrous sodium sulfate, and then subjected to suction filtration. The filtrate was concentrated to dryness to obtain an off-white solid, which was then purified by rapid ethanol-water recrystallization. The solid was dissolved with an appropriate amount of ethanol at 80° C., until it was just completely dissolved under the reflux of ethanol, then warm water was added thereto slowly under stirring to precipitate any solid until no more solid precipitated. Suction filtration was performed while the solution was still warm and the resulting system was thoroughly washed with warm water. The filter cake was dried to obtain 20.2 g of the compound (R)-BMSPINOL as a white solid, with a yield of 96%. $^{1}$H NMR (400 MHz, CDCl$_3$) δ 7.05 (s, 2H), 5.41 (s, 2H), 3.05 (s, 2H), 2.28 (d, J=13.0 Hz, 2H), 2.10 (d, J=13.0 Hz, 2H), 1.42 (s, 6H), 1.35 (s, 18H), 1.28 (s, 6H).

Under a nitrogen atmosphere, 19.6 g of the compound (R)-BMSPINOL was dissolved in 200 mL of ethyl acetate, and 18.3 g of N-bromosuccinimide (NBS) was added in batches. After stirring at room temperature for 16 hours, the reaction was completed. The obtained yellow solution was added with 50 mL of saturated sodium bisulfite solution, stirred vigorously for 30 minutes, and separated into different layers. The organic phase was washed with saturated sodium chloride solution, dried over anhydrous sodium sulfate, and then subjected to suction filtration. The filtrate was concentrated to dryness, and then recrystallized with methanol. 50 mL of methanol was added thereto, and the resulting system was refluxed for 5 minutes under stirring,

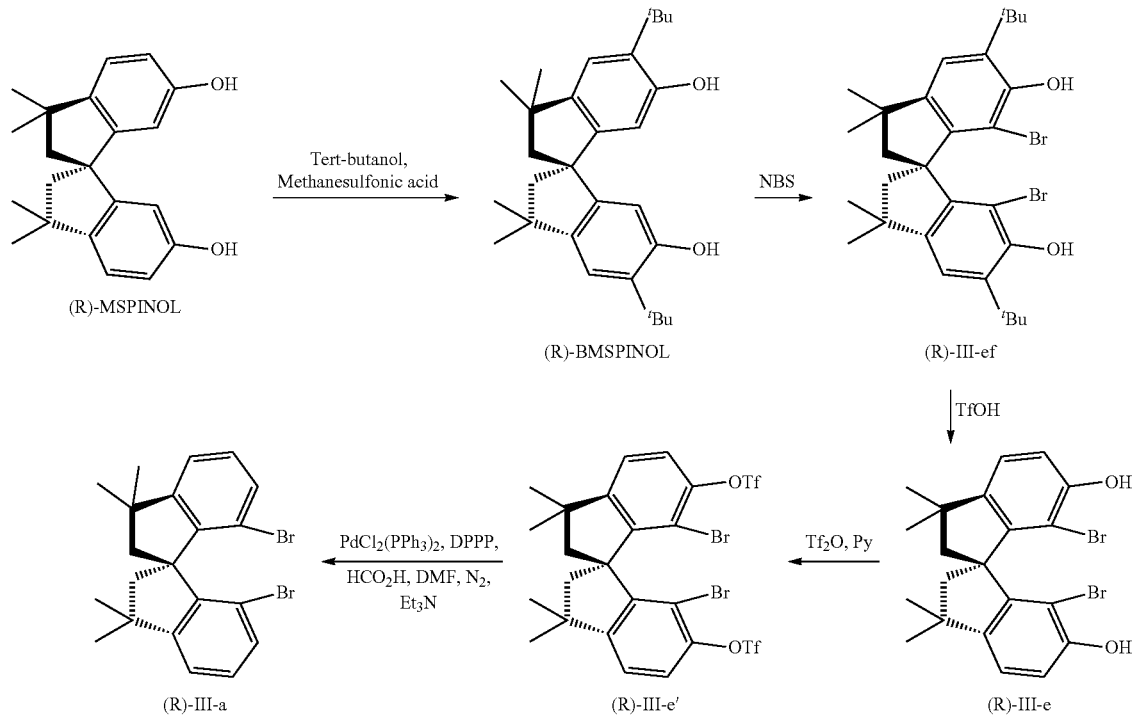

cooled to room temperature and then subjected to suction filtration. The filter cake was washed with a small amount of methanol and dried to obtain 25.4 g of the compound (R)-III-ef as a light yellow powder (with a yield of 90%); $^1$H NMR (400 MHz, CDCl$_3$) δ 6.98 (s, 2H), 5.80 (s, 2H), 2.49 (d, J=13.1 Hz, 2H), 2.25 (d, J=13.1 Hz, 2H), 1.41 (s, 18H), 1.39 (s, 6H), 1.32 (s, 6H).

15 g of the compound (R)-III-ef was added to a reaction flask and dissolved with 105 mL of toluene. Under cooling in an ice water bath, 2 mL of trifluoromethanesulfonic acid was added, and the reaction was conducted for 1 hour while stirring. The reaction was monitored by thin-layer chromatography (TLC) until completion. 30 mL of ice water was added to quench the reaction. The reaction solution was rotary-evaporated under reduced pressure to remove toluene and extracted with ethyl acetate, and then washed once respectively with saturated sodium chloride solution, saturated sodium bicarbonate solution and saturated sodium chloride solution sequentially. The organic phase was dried over anhydrous sodium sulfate and concentrated under reduced pressure to remove ethyl acetate. 30 mL of warm n-hexane was added to the concentrate, and the resulting system was refluxed under stirring for 15 minutes, cooled to room temperature, and then subjected to suction filtration. The filter cake was washed with n-hexane and dried to obtain 10.8 g of the compound (R)-III-e as a white powder, with a yield of 89%. $^1$H NMR (400 MHz, CDCl$_3$) δ 7.03 (d, J=8.2 Hz, 2H), 6.95 (d, J=8.2 Hz, 2H), 5.47 (s, 2H), 2.52 (d, J=13.1 Hz, 2H), 2.29 (d, J=13.1 Hz, 2H), 1.41 (s, 6H), 1.34 (s, 6H).

Under a nitrogen atmosphere, 8.8 g of the compound (R)-III-e, 40 mL of dichloromethane and 3.8 mL of pyridine were added to a reaction flask, stirred to dissolve, and cooled with an ice water bath. Then 6.5 mL of trifluoromethanesulfonic anhydride was slowly added dropwise. The reaction was performed under stirring at room temperature for 1 hour, and was monitored with TLC until completion. The reaction solution was washed sequentially with dilute hydrochloric acid, saturated sodium bicarbonate solution, and saturated sodium chloride solution. The organic phase was dried over anhydrous sodium sulfate and subjected to suction filtration. The filtrate was concentrated to dryness, and then purified by flash silica gel column chromatography to obtain 13.2 g of the compound (R)-III-e' as a white powder, with a yield of 96%. $^1$H NMR (400 MHz, CDCl$_3$) δ 7.26 (d, J=8.3 Hz, 2H), 7.19 (d, J=8.3 Hz, 2H), 2.59 (d, J=13.3 Hz, 2H), 2.36 (d, J=13.2 Hz, 2H), 1.45 (s, 6H), 1.39 (s, 6H).

Under a nitrogen atmosphere, 12 g of the compound (R)-III-e', 460 mg of bis(triphenylphosphine) palladium dichloride and 351 mg of 1,3-bis(diphenylphosphino)propane were added to a reaction flask. Then, 170 mL of N,N-dimethylformamide (DMF), 27 mL of triethylamine, and 4.8 mL of formic acid were sequentially injected into the reaction flask while stirring. The system was reacted under stirring at 80° C. for 80 minutes, and was monitored with TLC until the reaction was completed. After cooling to room temperature, 150 mL of water, 50 mL of dilute hydrochloric acid (3 M) and 200 mL of ethyl acetate were added to the reaction solution. The liquid was extracted, in which the aqueous phase was extracted again with ethyl acetate, and the organic phases were combined. The organic phase was washed with saturated sodium chloride solution, and then with 5 mL of hydrogen peroxide (30%) while shaking (to oxidize the phosphine ligand DPPP therein), and again with saturated sodium chloride solution. The organic phase was dried with anhydrous sodium sulfate, and concentrated under reduced pressure to obtain an off white solid. Finally, the off white solid was purified with flash column chromatography (200-300 mesh silica gel, E/P=1:20) to obtain 6.8 g of the compound (R)-III-a as a white solid (with a yield of 95%). $^1$H NMR (400 MHz, CDCl$_3$) δ 7.29 (dd, J=7.2, 1.2 Hz, 2H), 7.16-7.07 (m, 4H), 2.56 (d, J=13.1 Hz, 2H), 2.27 (d, J=13.1 Hz, 2H), 1.44 (s, 6H), 1.36 (s, 6H).

Example 2

Synthesis of (R)-3,3,5,3',3',5'-hexamethyl-7,7'-dibromo-1,1'-spirobiindane ((R)-III-b)

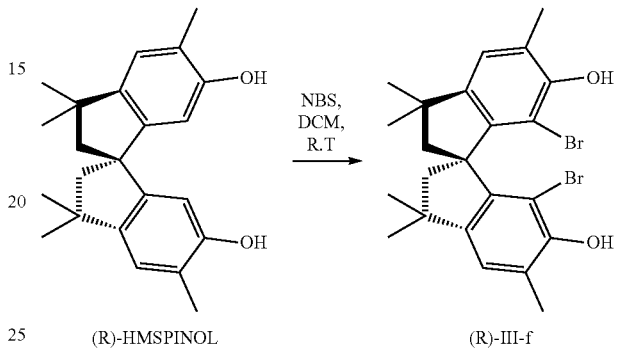

(R)-HMSPINOL          (R)-III-f

To a 500 mL three-necked flask, 18 g (R)-HMSPINOL and 200 mL of dichloromethane were added, and 19.8 g of N-bromosuccinimide was added in batches under electromagnetic stirring. The mixture was stirred for 1 hour at room temperature. The completion of the reaction was confirmed by TLC (petroleum ether:ethyl acetate=5:1). Excess amount of saturated sodium bisulfite solution was added and the stirring was continued for 1 hour. The liquid was separated, in which the aqueous phase was washed with 100 mL of dichloromethane, and the organic phases were combined and washed with saturated sodium chloride solution. The organic phase was dried over anhydrous sodium sulfate and subjected to suction filtration. After removal of the solvent from the filtrate, 26.4 g of the compound (R)-III-f was obtained as a light yellow powder with a yield of 99.8%, mp: 228° C. $^1$H NMR (400 MHz, CDCl$_3$) δ=6.88 (s, 2H), 2.47 (d, J=13.1 Hz, 2H), 2.31 (s, 6H), 2.25 (d, J=13.0 Hz, 2H), 1.39 (s, 6H), 1.33 (s, 6H). $^{13}$C NMR (101 MHz, CDCl$_3$) δ=149.25, 145.61, 142.67, 124.51, 123.60, 107.15, 60.85, 55.57, 43.06, 32.58, 29.28, 17.11; HRMS (EI-TOF): calcd for $C_{23}H_{26}Br_2O_2$ 492.0300, found 492.0302;

Single crystal data are as follows:
Cell: a=7.5979(5), b=14.0001(10), c=19.6290(12), alpha=90, beta=90, gamma=90; Temperature: 171 K
Space group P 21 21 21; Hall group P 2ac 2ab.

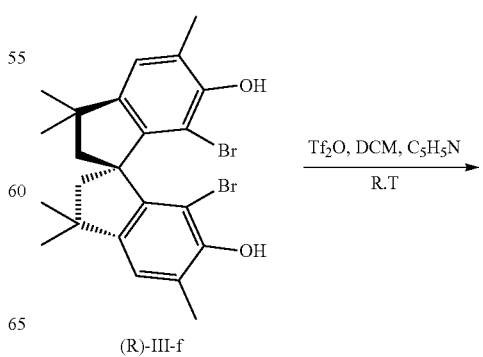

(R)-III-f

-continued

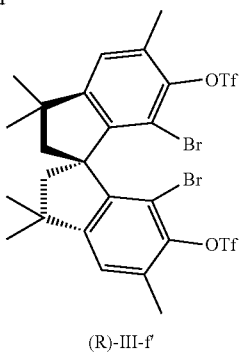

(R)-III-f'

To a three-necked flask, (R)-III-f (9 g, 18.2 mmol) was added under nitrogen protection, dichloromethane (150 mL) and pyridine (7.7 mL) were then added in sequence, and then trifluoromethanesulfonic anhydride (7.7 mL) was added slowly under an ice bath. The reaction was conducted while stirring at room temperature for 1 hour, and was monitored by TLC until completion. The reaction solution was washed sequentially with dilute hydrochloric acid, saturated sodium bicarbonate solution, and saturated sodium chloride solution. The organic phase was dried over anhydrous sodium sulfate and subjected to suction filtration. The filtrate was concentrated to dryness, and subjected to flash silica gel column chromatography (with a eluent of petroleum ether and ethyl acetate with a ratio of petroleum ether to ethyl acetate of 10:1), to obtain the compound (R)-III-f' as a white powder (13.2 g, with a yield of 96%), mp: 206° C. $^1$H NMR (400 MHz, CDCl$_3$): δ=7.02 (s, 2H), 2.55 (d, J=13.2 Hz, 2H), 2.45 (s, 6H), 2.30 (d, J=13.2 Hz, 2H), 1.42 (s, 6H), 1.36 (s, 6H); $^{19}$F NMR (400 MHz, CDCl$_3$): δ=−72.18 (s); $^{13}$C NMR (100 MHz, CDCl$_3$): δ=153.74, 145.12, 144.55, 132.61, 124.80, 123.33, 120.14, 116.95, 113.77, 113.37, 61.28, 54.92, 43.43, 32.37, 28.81, 18.16; HRMS (EI-TOF): calcd for C$_{25}$H$_{24}$F$_2$Br$_2$O$_2$S$_2$ 755.9285, found 755.9285.

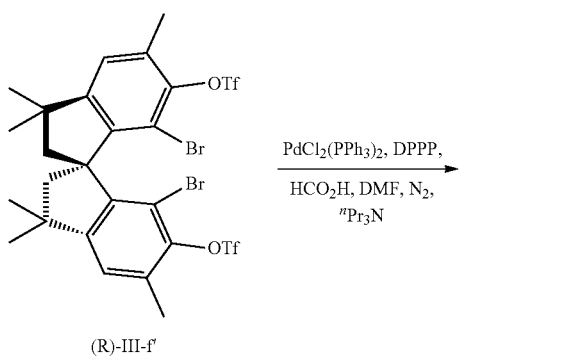

(R)-III-f'

(R)-III-b

To a three-necked flask, (R)-III-f' (12.9 g), bis(triphenylphosphine) palladium chloride (515 mg), and 1,3-bis(diphenylphosphino)propane (361 mg) were added under nitrogen protection, N,N-dimethylformamide (150 mL, DMF) and tripropylamine (38.5 mL) were added in sequence, and then formic acid (5.1 mL) was added slowly at 0° C. The reaction was conducted under stirring in an oil bath at 80° C. for 1 hour. After the reaction was completed, the solution was cooled to room temperature, and the reaction was quenched with water. Ethyl acetate was added to extract the liquid for separation. The aqueous phase was extracted with ethyl acetate again. The organic phases were combined, washed with 30% hydrogen peroxide solution for 5 minutes, and then washed sequentially with 4 mol/L HCl solution, saturated sodium bicarbonate solution and saturated sodium chloride solution. The organic phase was dried over anhydrous sodium sulfate, and subjected to suction filtration. The filtrate was concentrated to dryness, and then subjected to silica gel column flash column chromatography (with a eluent of petroleum ether and ethyl acetate with a ratio of petroleum ether to ethyl acetate of 50:1) to obtain the compound (R)-III-b as a white powder, with a yield of 95%, mp: 202° C. $^1$H NMR (400 MHz, CDCl$_3$): δ=7.18 (s, J=7.4 Hz, 2H), 6.97 (s, 2H), 2.57 (d, J=13.1 Hz, 2H), 2.38 (s, 6H), 2.28 (d, J=13.1 Hz, 2H), 1.43 (s, 6H), 1.38 (s, J=8.2 Hz, 6H); $^{13}$C NMR (100 MHz, CDCl$_3$): δ=154.92, 142.48, 138.92, 131.88, 122.32, 119.14, 59.79, 55.36, 43.42, 32.56, 28.94, 20.98.

Example 3

Synthesis of 3,3,3',3'-tetramethyl-5,5'-di-tert-butyl-7,7'-diiodo-1,1'-spirobiindane-6,6'-diol (III-bg)

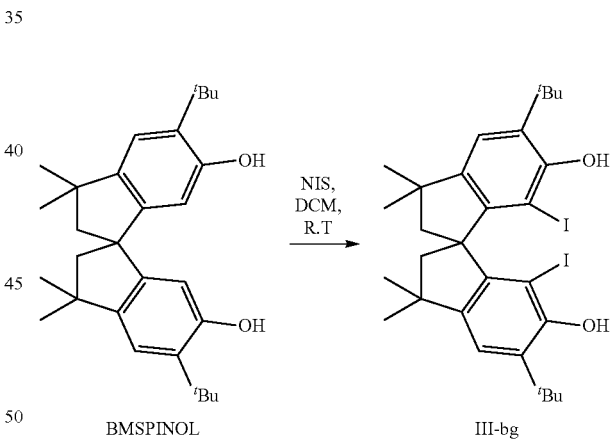

BMSPINOL                III-bg

To a reaction flask, 1.5 g of HMSPINOL, 0.15 g of p-toluenesulfonic acid, and 45 mL of dichloromethane were added, and 2.1 g of N-iodosuccinimide was added slowly under magnetic stirring. The mixture was reacted under stirring at room temperature for 6 hours until TLC (petroleum ether:ethyl acetate=5:1) confirmed the completion of the reaction. Excessive amount of saturated sodium disulfite solution was added and the stirring was continued for 1 hour. The liquid was separated, and the aqueous phase was washed with 20 mL of dichloromethane. The organic phases were combined, washed with saturated sodium chloride solution, dried over anhydrous sodium sulfate, and subjected to suction filtration. After removal of the solvent from the filtrate, 2.24 g of the compound III-bg was obtained as a powder. $^1$H NMR (400 MHz, CDCl$_3$) δ 7.01 (s, 2H), 5.68 (s, 2H), 2.45 (d, J=13.1 Hz, 2H), 2.25 (d, J=13.1 Hz, 2H), 1.42 (s, 6H), 1.41 (s, 18H), 1.33 (s, 6H).

Example 4

Synthesis of 3,3,5,3',3',5'-hexamethyl-7,7'-diiodo-1,1'-spirobiindane-6,6'-diol (III-g)

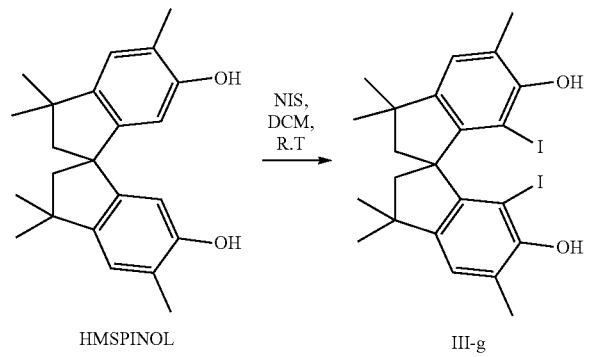 [SMILES: Cc1cc2c(cc1O)C1(CC2(C)C)CC(C)(C)c2cc(C)c(O)cc21 ; Cc1cc2c(c(I)c1O)C1(CC2(C)C)CC(C)(C)c2cc(C)c(O)c(I)c21]

To a reaction flask, 1.5 g of HMSPINOL, 0.195 g of p-toluenesulfonic acid, 45 mL of dichloromethane were added, and 2.254 g of N-iodosuccinimide was added slowly under magnetic stirring. The mixture was stirred at room temperature for 5 hours until TLC (petroleum ether: ethyl acetate=5:1) confirmed the completion of the reaction. Excessive amount of saturated sodium bisulfite solution was added and the stirring was continued for 1 hour. The liquid was separated, and the aqueous phase was washed with 20 mL of dichloromethane. The organic phases were combined, washed with saturated sodium chloride solution, dried over anhydrous sodium sulfate, and subjected to suction filtration. After removal of the solvent from the filtrate, 2.44 g of the compound III-g was obtained as a yellow powder, with a yield of 93%.

Example 5

Synthesis of (R)-3,3,3',3'-tetramethyl-6,6'-dimethoxy-7,7'-dibromo-1,1'-spirobiindane (III-j)

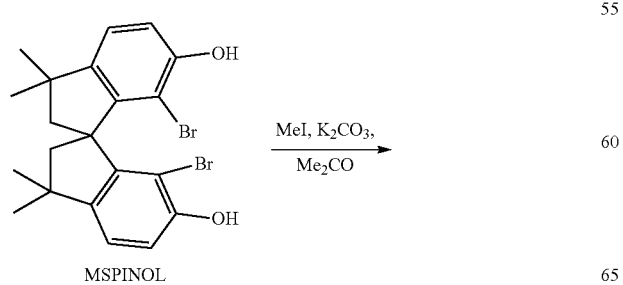

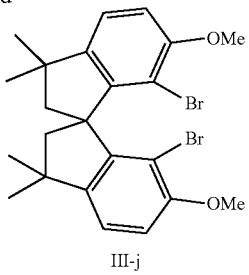

To a reaction flask, 3 g of MSPINOL, 3.56 g of potassium carbonate, 30 mL of acetone, and 1.6 mL of methyl iodide were added. The reaction solution was warmed up to 35° C., and reacted under stirring for 12 hours until TLC monitored that the raw materials were disappeared and completely became a product. 60 mL of concentrated ammonia water was added and the stirring was continued for 2 hours. After being cooled to room temperature, the solution was subjected to suction filtration, washed with warm water 3 times, and dried to obtain 3.04 g of the compound III-j as a white powder, with a yield of 96%. $^1$H NMR (400 MHz, CDCl$_3$) δ 7.08 (dd, J=8.2, 4.4 Hz, 2H), 6.82 (dd, J=8.2, 4.4 Hz, 2H), 3.85 (6H), 2.61 (d, J=13.0 Hz, 2H), 2.27 (d, J=13.0 Hz, 2H), 1.42 (s, 6H), 1.35 (s, 6H).

Example 6

Synthesis of (R)-3,3,5,3',3',5'-hexamethyl-6,6'-diphenyl-7,7'-dibromo-1,1'-spirobiindane ((R)-III-fff)

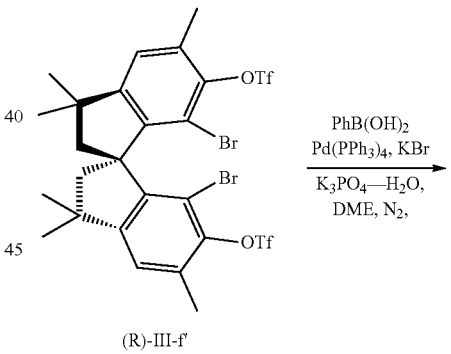

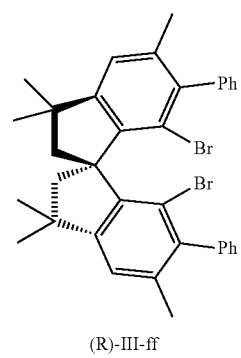

Under nitrogen protection, (R)-III-f' (0.22 g), phenylboronic acid (0.3 g), potassium bromide (0.1 g), and tetrakis (triphenylphosphine) palladium (50 mg) were added to a reaction flask, and then 2 mL of ethylene glycol dimethyl ether (DME), 1 mL of water and 0.45 g of potassium phosphate trihydrate were added. The reaction was performed under stirring at 90° C. for 24 hours. After the reaction was completed, the reaction was quenched with water, and the resulting system was extracted with ethyl acetate, dried over anhydrous sodium sulfate, and subjected to suction filtration.

The filtrate was concentrated to dryness and purified with flash silica gel column chromatography to obtain the compound (R)-III-fff as a powder, with a yield of 55%.

Example 7

Synthesis of (R)-3,3,3',3'-tetramethyl-7,7'-diiodo-1, 1'-spirobiindane ((R)-III-aa)

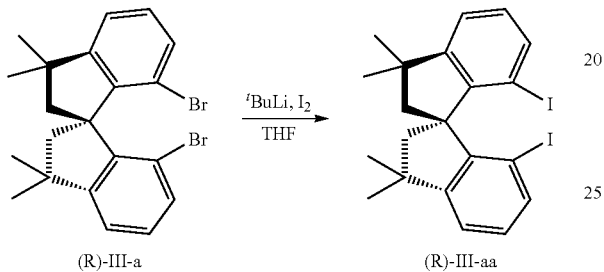

Under a nitrogen atmosphere, (R)-III-a (1 g) and 10 mL of anhydrous degassed tetrahydrofuran were added to a flask and cooled to −78° C., and then a solution of tert-butyllithium in n-hexane (8 mL, 2 mol/L) was added dropwise. The reaction was performed under stirring for 1 hour, and iodine (10 mmol) was added, and then the reaction solution was naturally warmed up to room temperature and reacted overnight. The reaction was quenched with water, and the resulting system was extracted with ethyl acetate, dried over anhydrous sodium sulfate, and subjected to suction filtration. The filtrate was concentrated to dryness and purified with flash silica gel column chromatography to obtain the compound (R)-III-aa, with a yield of 80%. $^1$H NMR (400 MHz, CDCl$_3$) δ 7.63 (dd, J=7.7, 0.9 Hz, 2H), 7.19 (dd, J=7.5, 0.9 Hz, 2H), 6.94 (dd, J=14.4, 6.8 Hz, 2H), 2.49 (d, J=13.1 Hz, 2H), 2.27 (d, J=13.0 Hz, 2H), 1.47 (s, 6H), 1.36 (s, 6H).

What is claimed is:

1. A 7,7'-dihalo-3,3,3',3'-tetramethyl-1,1'-spirobiindane, being a compound represented by formula I, or an enantiomer, a raceme or a diastereomer thereof:

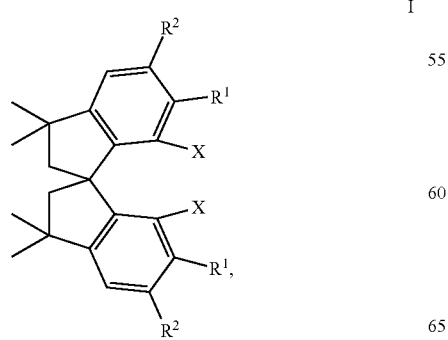

wherein $R^1$ is selected from the group consisting of hydrogen, $C_1$-$C_{10}$ alkyl or perfluoroalkyl, $C_3$-$C_6$ cycloalkyl, aryl or substituted aryl, and heteroaryl or substituted heteroaryl; $R^2$ is selected from the group consisting of hydrogen, $C_1$-$C_{10}$ alkyl or perfluoroalkyl, and $C_3$-$C_6$ cycloalkyl; wherein the substituted aryl or the substituted heteroaryl has one or more substituents independently selected from the group consisting of halogen, $C_1$-$C_4$ alkyl or perfluoroalkyl, $C_3$-$C_6$ cycloalkyl, $C_1$-$C_4$ alkoxy or perfluoroalkoxy, methylenedioxy, aryl, aryloxy, and heteroaryl; the heteroaryl is $C_5$-$C_{14}$ heteroaryl; and X is halogen.

2. The 7,7'-dihalo-3,3,3',3'-tetramethyl-1,1'-spirobiindane according to claim 1, wherein the compound represented by formula I is any one of the following compounds:

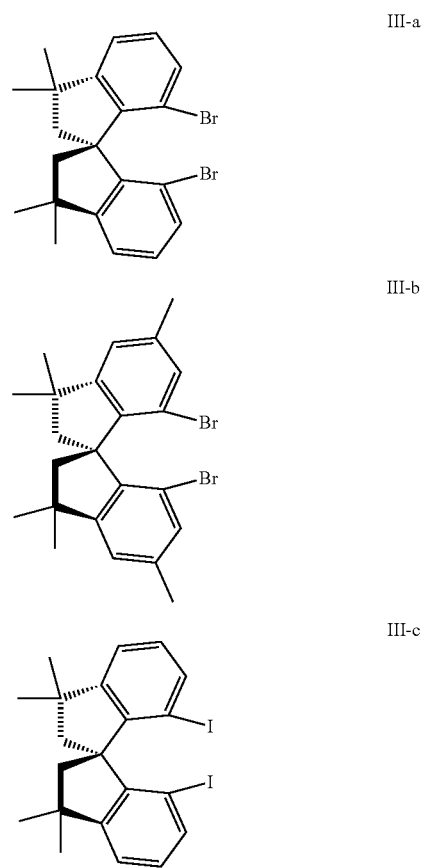

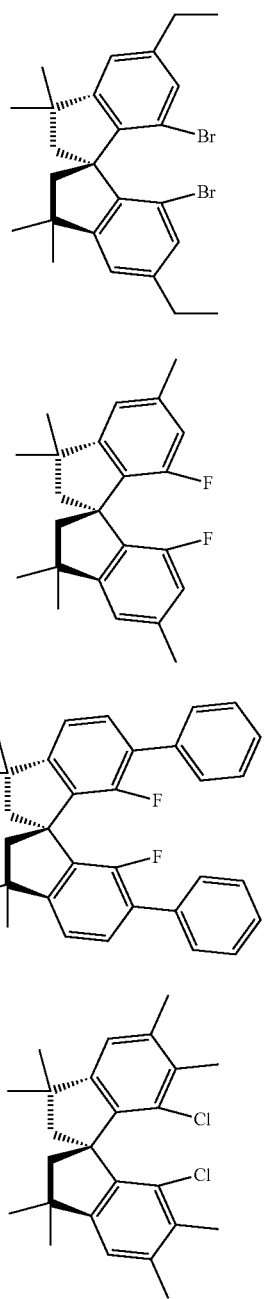

III-ee

III-ff

III-gg

III-hh

III-i

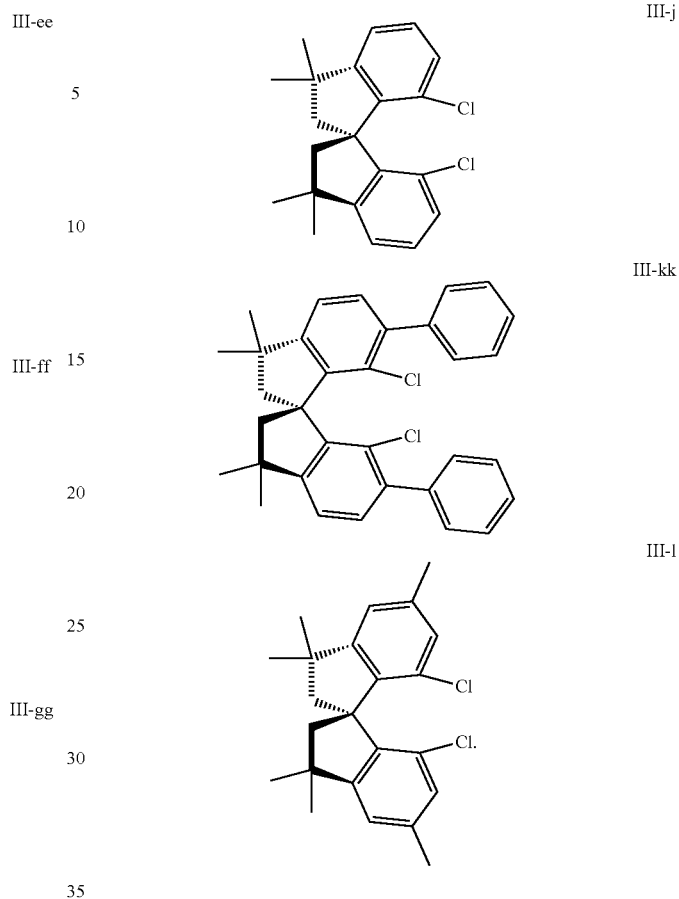

III-j

III-kk

III-l

3. A method for preparing the compound represented by formula I according to claim 1, comprising using a racemic or optically active 3,3,3',3'-tetramethyl-1,1'-spirobiindane-6,6'-diol represented by formula 1 as a raw material, and the following steps:

under the condition that $R^2$ is selected from $C_1$-$C_{10}$ alkyl or perfluoroalkyl and $C_3$-$C_6$ cycloalkyl, subjecting a compound represented by formula 1 to a halogenation reaction to obtain a compound 2, subjecting the compound 2 to an esterification reaction with trifluoromethanesulfonic anhydride to obtain a compound 3, and then subjecting the compound 3 to a palladium-catalyzed coupling reaction or a reduction reaction to obtain the compound represented by formula I;

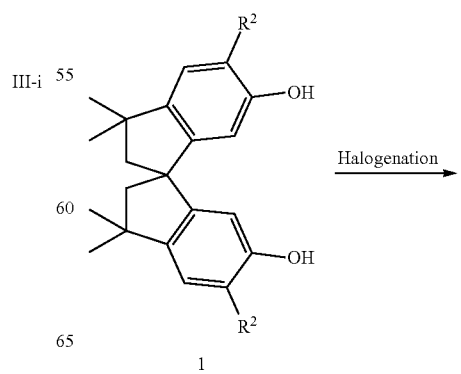

1

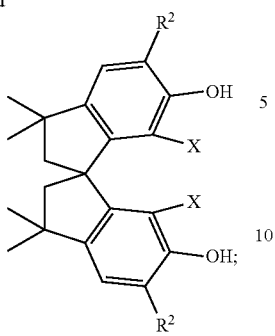

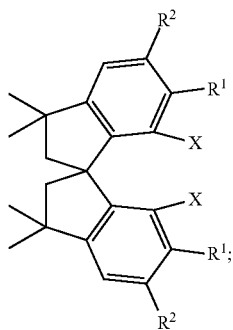

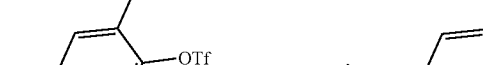

or under the condition that $R^2$ is hydrogen, subjecting the compound represented by formula 1 to a tert-butylation reaction to obtain a compound A2, subjecting the compound A1 to a halogenation reaction to obtain a compound 4, subjecting the compound 4 to a tert-butyl elimination reaction to obtain a compound 5, subjecting the compound 5 to an esterification reaction with trifluoromethanesulfonic anhydride to obtain a compound 6, and then subjecting the compound 6 to a palladium-catalyzed coupling reaction or a reduction reaction to obtain the compound represented by formula I;

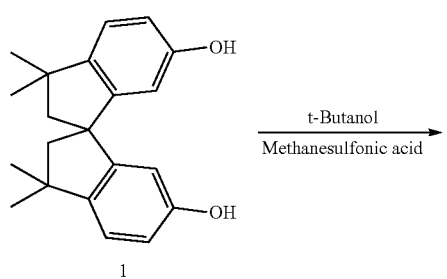

-continued
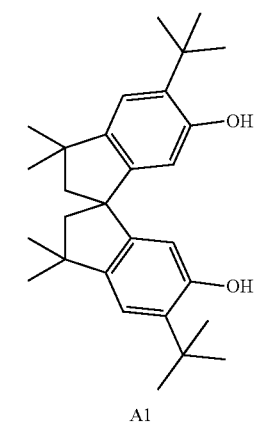
A1
Halogenation →
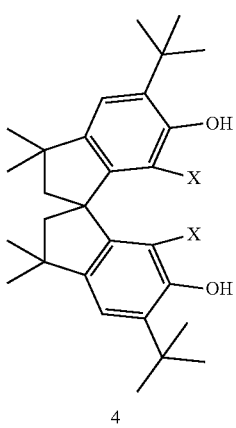
4
Trifluoromethane-
sulfonic acid →
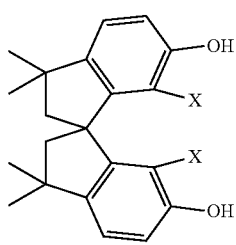
5
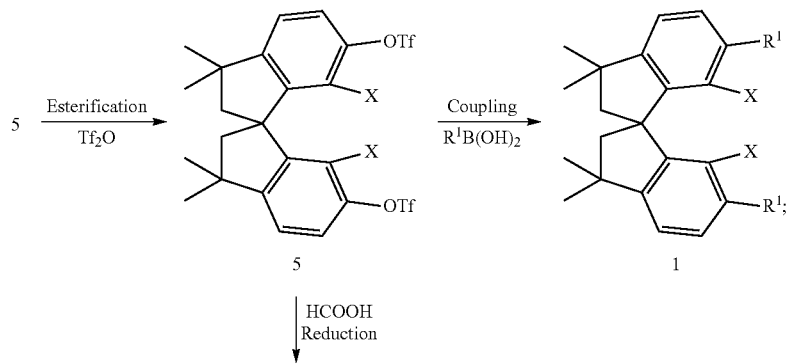

-continued
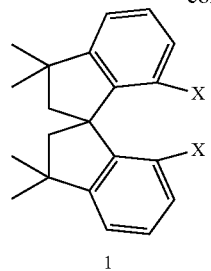
wherein X is halogen, and $R^1$ is as defined in claim 1.
* * * * *